United States Patent [19]

Harada et al.

[11] Patent Number: 4,506,011

[45] Date of Patent: Mar. 19, 1985

[54] PROCESS FOR PREPARATION OF ASPARTYLPHENYLALANINE ALKYL ESTERS

[75] Inventors: Tsuneo Harada, Tokuyama; Hisao Takemoto, Nanyo; Tatsuo Igarashi, Tokuyama, all of Japan

[73] Assignee: Toyo Soda Manufacturing Co., Ltd., Nanyo, Japan

[21] Appl. No.: 411,628

[22] Filed: Aug. 26, 1982

[30] Foreign Application Priority Data

Sep. 5, 1981 [JP] Japan ................................. 56-139247
Oct. 14, 1981 [JP] Japan ................................. 56-162697
Jan. 18, 1982 [JP] Japan ..................................... 57-4830

[51] Int. Cl.$^3$ ........................ C12P 21/02; C12R 1/05; C12R 1/40; C12R 1/645; C12R 1/88
[52] U.S. Cl. ..................................... 435/70; 435/829; 435/877; 435/911; 435/944
[58] Field of Search ................... 435/68, 70, 174, 829, 435/874, 877, 944, 911, 822

[56] References Cited

U.S. PATENT DOCUMENTS 4,119,493 10/1978 Isowa et al. ........................... 435/70
4,284,721 8/1981 Oyama et al. ......................... 435/70

FOREIGN PATENT DOCUMENTS 74095 3/1983 European Pat. Off. .............. 435/70

*Primary Examiner*—Esther M. Kepplinger
*Attorney, Agent, or Firm*—Cushman, Darby & Cushman

[57] ABSTRACT

α-L-aspartylphenylalanine lower alkyl esters are prepared by a process wherein L-aspartic acid and a lower alkyl ester of L-phenylalanine are contacted with a culture or treated culture product of a microorganism belonging to the genus Pseudomonas, Alcaligenes, Torulopsis, Rhodotorula or Sporobolomyces and being capable of producing a α-L-aspartyl-L-phenylalanine lower alkyl ester from L-aspartic acid and a lower alkyl ester of L-phenylalanine.

10 Claims, No Drawings

PROCESS FOR PREPARATION OF ASPARTYLPHENYLALANINE ALKYL ESTERS

BACKGROUND OF THE INVENTION (1) Field of the Invention

This invention relates to a process for the preparation of aspartylphenylalanine alkyl esters.

(2) Description of the Prior Art

An α-L-aspartyl-L-phenylalanine lower alkyl ester (hereinafter referred to as "α-APE" for brevity), especially α-L-aspartyl-L-phenylalanine methyl ester, is a valuable substance as a novel sweetening agent.

Several processes for the preparation of the α-APE are known. In one process, an N-protected-L-aspartic anhydride is reacted with a lower alkyl ester of L-phenylalanine to form an N-protected-α-APE and then the protecting group is removed to form an α-APE. In another process, an N-protected-L-aspartic acid is reacted with a lower alkyl ester of phenylalanine in the presence of a protease to form an N-protected-α-APE or an adduct of N-protected-α-APE with the lower alkyl ester of phenylalanine, and then, the protecting group is removed to form an α-APE.

The former process has a problem in that an N-protected-β-APE is formed as a by-product together with the N-protected-α-APE. The latter process is advantageous in that the above problem does not rise and a lacemic mixture can be used as the starting compound. In each process, however, the starting aspartic acid or its anhydride should be used after the amino group has been protected with a protecting group such as a benzyloxycarbonyl group.

If the steps of introducing and removing an amino group-protecting group, which are indispensable in the conventional processes, can be omitted, this could be very advantageous from the industrial viewpoint because the steps of the process are simplified and the loss of the starting and intended compounds is minimized.

SUMMARY OF THE INVENTION

It is therefore a primary object of the present invention to provide a process for preparing an α-APE wherein the intended α-APE can be prepared directly from L-aspartic acid and a lower alkyl ester of L-phenylalanine by simplified process steps.

More specifically, in accordance with the present invention, a process is provided a process for the preparation of aspartylphenylalanine alkyl esters, which comprises contacting a culture or treated culture product of a microorganism belonging to the genus Pseudomonas, Alcaligenes, Torulopsis, Rhodotorula or Sporobolomyces and being capable of producing a lower alkyl ester of α-L-aspartyl-L-phenylalanine from L-aspartic acid and a lower alkyl ester of L-phenylalanine, with L-aspartic acid and a lower alkyl ester of L-phenylalanine.

DESCRIPTION OF THE PREFERRED EMBODIMENTS

Microorganisms used in the present invention are α-APE-producing species belonging to the above-mentioned genera. The taxonomical properties of these microorganisms, which have been separated from soil or flowers in Shin-Nanyo city, Yamaguchi prefecture, Japan, will now be described.

*Pseudomonas putida* TS-15001

Separation source: soil (A) Morphology: Cultivation on a nutrient broth agar culture medium (after incubation at 37° C. for 6 to 24 hours).
  (1) Cell form and cell size: rods, (0.5 to 0.7) $\mu \times$ (1.0 to 1.5) $\mu$
  (2) Arrangement: single or pair
  (3) Motility: motile by polar flagella
  (4) Endospore: none
  (5) Gram stainity: negative
  (6) Acid fastness: negative (B) Cultural characteristics:
  (1) Cultivation on a nutrient broth agar plate (after incubation at 37° C. for 2 days).
    (a) Colony formation rate: moderate, about 6 mm in diameter
    (b) Colony form: circular
    (c) Colony surface: smooth
    (d) Elevation of growth: convex
    (e) Edge of colony: entire
    (f) Content of colony: amorphous
    (g) Tint of colony: milky white
    (h) Transmittance of colony: translucent
    (i) Glistening of colony: dull
    (j) Formation of soluble coloring material: soluble light-green pigment formed
  (2) Cultivation on a nutrient broth agar slant (after incubation at 37° C. for 2 days)
    (a) Growth: good
    (b) Colony form: smooth
    (c) Elevation of growth: flat
    (d) Glistening of colony: dull
    (e) Colony surface: smooth
    (f) Transmittance of colony: translucent
    (g) Tint of colony: milky white
    (h) Content of colony: butyrous
  (3) Cultivation on a nutrient broth medium (after incubation at 37° C. for 2 days)
    (a) Growth on surface: none
    (b) Turbidity: moderately turbid
    (c) Precipitate formation: compact
    (d) Generation of gas: negative
    (e) Coloration of medium: negative
  (4) Cultivation on a nutrient broth agar stab (after incubation at 37° C. for 2 days)
    (a) Location of growth: uniform
    (b) Form of colony: papillate
  (5) Cultivation on a nutrient broth gelatin stab (after inculation at 20° C. for 14 days)
    (a) Liquefaction of gelatin: negative
  (6) Cultivation on a litmus milk medium (after incubation at 37° C. for 7 days)
    (a) Reaction: BCP blued, litmus changed to bluish violet
    (b) Coagulation or liquefaction: negative (C) Physiological properties:
  (a) Reduction of nitrate: negative
  (b) Denitrification: negative
  (c) MR test: negative
  (d) VP test: negative
  (e) Formation of indole: negative
  (f) Formation of hydrogen sulfide: positive (W)
  (g) Hydrolysis of starch: negative
  (h) Utilization of citric acid: positive
  (i) Utilization of inorganic nitrogen source: only ammonia nitrogen utilized (j) Formation of coloring material: soluble greenish yellow fluorescent pigment
(k) Urease: negative
(l) Oxidase: positive
(m) Catalase: positive
(n) Range for growth: pH value of from 5 to 9.5, temperature of from 10° to 43° C.
(o) Oxygen requirement: aerobic
(p) O-F test: oxidative
(q) Formation of acid or gas from saccharides:

|  | Acid | Gas |
|---|---|---|
| (1) L-Arabinose | + | − |
| (2) D-Xylose | + | − |
| (3) D-Glucose | + | − |
| (4) D-Mannose | + | − |
| (5) D-Fructose | − | − |
| (6) D-Galactose | + | − |
| (7) Maltose | − | − |
| (8) Sucrose | − | − |
| (9) Lactose | − | − |
| (10) Trehalose | − | − |
| (11) D-Sorbit | − | − |
| (12) D-Mannit | − | − |
| (13) Inosit | − | − |
| (14) Glycerin | − | − |
| (15) Starch | − | − |

(r) Arginine dihydrolase: positive
(s) Utilization of carbon sources (after incubation at 37° C. for 1 to 7 days): Carbon sources utilized: D-glucose, L-valine, β-L-alanine and L-arginine Carbon sources not utilized: trehalose, meso-inositol and geraniol

*Alcaligenes faecalis* TS-15002

Separation source: soil
(A) Morphology:
Cultivation on a nutrient broth agar culture medium (after incubation at 37° C. for 6 to 24 hours)
  (1) Cell form and cell size: rods, (0.5 to 0.8) $\mu \times$ (1.0 to 1.5) $\mu$
  (2) Arrangement: single or pair
  (3) Motility: motile by peripheral flagella
  (4) Endospore: none
  (5) Gram stainity: negative
  (6) Acid fastness: negative
(B) Cultural characteristics:
  (1) Cultivation on a nutrient broth agar plate (after incubation at 37° C. for 4 days)
    (a) Colony formation rate: slow, about 2 mm in diameter
    (b) Colony form: circular
    (c) Colony surface: smooth
    (d) Elevation of growth: convex
    (e) Edge of colony: entire
    (f) Content of colony: amorphous
    (g) Tint of colony: milky white
    (h) Transmittance of colony: translucent
    (i) Glistening of colony: dull
    (j) Formation of soluble coloring material: none
  (2) Cultivation on a nutrient broth agar slant (after incubation at 37° C. for 2 days)
    (a) Growth: good
    (b) Form of colony: smooth
    (c) Elevation of growth: flat
    (d) Glistening of colony: dull
    (e) Colony surface: smooth
    (f) Transmittance of colony: translucent
    (g) Tint of colony: milky white
    (h) Content of colony: butyrous
  (3) Cultivation on a nutrient broth medium (after incubation at 37° C. for 2 days)
    (a) Growth on surface: none
    (b) Turbidity: moderately turbid
    (c) Formation of precipitate: compact
    (d) Generation of gas: negative
    (e) Coloration of medium: negative
  (4) Cultivation on a nutrient broth agar stab (after incubation at 37° C. for 2 days)
    (a) Location of growth: uniform
    (b) Form of colony: papillate
  (5) Cultivation on a nutrient broth gelatin stab (after incubation at 37° C. and 20° C. for 14 days)
    (a) Liquefaction of gelatin: negative
  (6) Cultivation on a litmus milk medium (after incubation at 37° C. for 7 days)
    (a) Reaction: BCP blued, litmus changed to bluish violet from pink
    (b) Coagulation or liquefaction: negative
(C) Physiological properties:
  (a) Reduction of nitrate: negative
  (b) Denitrification: negative
  (c) MR test: negative
  (d) VP test: negative
  (e) Formation of indol: negative
  (f) Formation of hydrogen sulfide: negative
  (g) Hydrolysis of starch: negative
  (h) Utilization of citric acid: positive
  (i) Utilization of inorganic nitrogen source: only ammonia nitrogen utilized
  (j) Formation of dye: negative
  (k) Urease: negative
  (l) Oxidase: positive
  (m) Catalase: positive (W)
  (n) Range for growth: pH value of from 5 to 8.8, temperature of from 11° to 41° C.
  (o) Oxygen requirement: aerobic
  (p) O-F test: oxidative
  (q) Formation of acid or gas from saccharides:

|  | Acid | Gas |
|---|---|---|
| (1) L-Arabinose | − | − |
| (2) D-Xylose | + | − |
| (3) D-Glucose | − | − |
| (4) D-Mannose | − | − |
| (5) D-Fructose | − | − |
| (6) D-Galactose | − | − |
| (7) Maltose | − | − |
| (8) Sucrose | − | − |
| (9) Lactose | − | − |
| (10) Trehalose | − | − |
| (11) D-Sorbit | − | − |
| (12) D-Mannit | − | − |
| (13) Inosit | − | − |
| (14) Glycerin | − | − |
| (15) Starch | − | − |

*Torulopsis candida* TS-15101

Separation source: flower
(A) Morphology:
  (1) Cultivation on an MY agar plate (after incubation at 25° C.)
    (a) Form of trophocyte: oval
    (b) Size of trophocyte: (3 to 5) $\mu \times$ (4 to 8) $\mu$
    (c) Mode of propagation: multipolar budding without hypha or pseudohypha (2) Cultivation on an MY liquid medium (after incubation at 25° C. for 7 days)
  (a) Formation of gas: negative
  (b) Growth on surface: ring
  (c) Turbidity of medium: moderately turbid
  (d) Formation of precipitate: compact
  (e) Coloration of medium: negative
(3) Cultivation on an MY agar slant (after incubation at 25° C. for 30 days)
  (a) Growth: good
  (b) Edge of colony: wavy
  (c) Elevation of colony: convex
  (d) Surface of colony: smooth
  (e) Glistening of colony: dull
  (f) Content of colony: butyrous
  (g) Tint of colony: white
(4) Cultivation on a potate slide Formation of hypha or pseudohypha: not observed
(B) Formation of ascospore: Not observed
(C) Formation of ballistospore: Not observed
(D) Physiological properties:
  (a) Optimum growth conditions: pH value of from 3 to 7.5, temperature of from 15° to 30° C.
  (b) Range for growth: pH value of from 3 to 8.2, temperature of 5° to 37° C.
  (c) Assimilation of nitrate: negative
  (d) Decomposition of fat: positive (weak)
  (e) Decomposition of urea: negative
  (f) Liquefaction of gelatin: positive
  (g) Formation of carotenoid dye: negative
  (h) Prominent formation of organic acid: negative
  (i) Formation of starch analogue: negative
  (j) Vitamin requirement: positive (biotinrequiring)
(E) Assimilation of carbohydrates (after incubation at 25° C. for 7 days in Wickerham medium):

|     |                | Assimilation | Fermentation |
| --- | -------------- | ------------ | ------------ |
| (a) | D-Arabinose    | −            |              |
| (b) | L-Arabinose    | −            |              |
| (c) | D-Xylose       | + (W)        |              |
| (d) | D-Glucose      | +            | +            |
| (e) | D-Galactose    | + (W)        | −            |
| (f) | Maltose        | +            | −            |
| (g) | Sucrose        | +            | −            |
| (h) | Lactose        | −            | −            |
| (i) | Trehalose      | +            |              |
| (j) | Raffinose      | +            | −            |
| (k) | α-Methyl-D-glucoside | + (W)  |              |
| (l) | Soluble starch | + (W)        |              |
| (m) | Ethanol        | −            |              |
| (n) | Inosit         | −            |              |
| (o) | D-Mannit       | +            |              |
| (p) | D-Sorbit       | +            |              |
| (q) | Glycerin       | +            |              |
| (r) | Citric acid    | −            |              |

*Rhodotorula glutinis* TS15103

Separation source: flower
(A) Morphology:
  (1) Cultivation on an MY agar plate (after incubation at 25° C.)
    (a) Form of trophocyte: oval
    (b) Size of trophocyte: (3 to 5) μ×(8 to 10) μ
    (c) Mode of propagation: multipolar budding without hypha or pseudohypha
  (2) Cultivation on an MY liquid medium (after incubation at 25° C. for 7 days)
    (a) Formation of gas: negative
    (b) Growth on surface: smooth
    (c) Turbidity of medium: moderately turbid
    (d) Formation of precipitate: compact
    (e) Coloration of medium: negative
  (3) Cultivation on an MY agar slant (after incubation at 25° C. for 30 days)
    (f) Growth: good
    (g) Edge of colony: entire
    (h) Elevation of colony: convex
    (i) Surface of colony: smooth
    (j) Glistening of colony: dull
    (k) Content of colony: butyrous
    (l) Tint of colony: white
  (4) Cultivation on a potate slide Formation of hypha or pseudohypha: not observed
(B) Formation of ascospore: not observed
(C) Formation of ballistospore: not observed
(D) Physiological properties:
  (a) Optimum growth conditions: pH value of from 3 to 7.5, temperature of from 15° to 30° C.
  (b) Range for growth: pH value of from 3 to 8.2, temperature of 1° to 35° C.
  (c) Assimilation of nitrate: positive
  (d) Decomposition of fat: positive
  (e) Decomposition of urea: positive
  (f) Liquefaction of gelatin: positive
  (g) Formation of carotenoid dye: positive (red)
  (h) Prominent formation of organic acid: negative
  (i) Formation of starch analogue: negative
  (j) Vitamin requirement: negative
(E) Assimilation of carbohydrates (after incubation at 25° C. for 7 days in Wickerham medium):

|     |                | Assimilation | Fermentation |
| --- | -------------- | ------------ | ------------ |
| (a) | D-Arabinose    | +            |              |
| (b) | L-Arabinose    | +            |              |
| (c) | D-Xylose       | +            |              |
| (d) | D-Glucose      | +            | −            |
| (e) | D-Galactose    | +            | −            |
| (f) | Maltose        | +            | −            |
| (g) | Sucrose        | +            | −            |
| (h) | Lactose        | −            | −            |
| (i) | Trehalose      | +            |              |
| (j) | Raffinose      | +            | −            |
| (k) | α-Methyl-D-glucoside | +      |              |
| (l) | Soluble starch | +            |              |
| (m) | Ethanol        | −            | −            |
| (n) | Inosit         | −            |              |
| (o) | D-Mannit       | +            |              |
| (p) | D-Sorbit       | +            |              |
| (q) | Glycerin       | +            |              |
| (r) | Citric acid    | −            |              |

*Sporobolomyces odorus* TS-15105

Separation source: flower
(A) Morphology:
  (1) Cultivation on an MY agar plate (after incubation at 25° C.)
    (a) Form of trophocyte: cylindrical
    (b) Size of trophocyte: (3 to 5) μ×(6 to 10) μ
    (c) Mode of propagation: multipolar budding without hypha or pseudohypha
  (2) Cultivation on an MY liquid medium (after incubation at 25° C. for 7 days)
    (a) Formation of gas: negative
    (b) Growth on surface: smooth
    (c) Turbidity of medium: moderately turbid
    (d) Formation of precipitate: compact (e) Coloration of medium: negative
(3) Cultivation on an MY agar slant (after incubation at 25° C. for 30 days)
  (a) Growth: good
  (b) Edge of colony: entire
  (c) Elevation of colony: convex
  (d) Surface of colony: smooth
  (e) Glistening of colony: dull
  (f) Content of colony: butyrous
  (g) Tint of colony: orange
(4) Cultivation on a potate slide Formation of hypha or pseudohypha: not observed
(B) Formation of ascospore: Not observed
(C) Formation of ballistospore: Not observed
(D) Physiological properties:
  (a) Optimum growth conditions: pH value of from 3 to 7.5, temperature of from 20° to 33° C.
  (b) Range for growth: pH value of from 3 to 8.2, temperature of 14° to 36° C.
  (c) Assimilation of nitrate: positive
  (d) Decomposition of fat: negative
  (e) Decomposition of urea: positive
  (f) Liquefaction of gelatin: negative
  (g) Formation of carotenoid dye: positive (orange)
  (h) Prominent formation of organic acid: negative
  (i) Formation of starch analogue: negative
  (j) Vitamin requirement: negative
(E) Assimilation of carbohydrates (after incubation at 25° C. for 7 days in Wickerham medium):

|     |               | Assimilation | Fermentation |
| --- | ------------- | ------------ | ------------ |
| (a) | D-Arabinose   | +            |              |
| (b) | L-Arabinose   | +            |              |
| (c) | D-Xylose      | +            |              |
| (d) | D-Glucose     | +            | −            |
| (e) | D-Galactose   | +            | −            |
| (f) | Maltose       | −            | −            |
| (g) | Sucrose       | +            | −            |
| (h) | Lactose       | −            | −            |
| (i) | Trehalose     | +            |              |
| (j) | Raffinose     | +            | −            |
| (k) | α-Methyl-D-glucoside | +     |              |
| (l) | Soluble starch | +           |              |
| (m) | Ethanol       | −            |              |
| (n) | Inosit        | −            |              |
| (o) | D-Mannit      | +            |              |
| (p) | D-Sorbit      | +            |              |
| (q) | Glycerin      | +            |              |
| (r) | Citric acid   | + (W)        |              |

All of the foregoing strains were deposited on June 21, 1981 at the Fermentation Research Institute (FERM), Agency of Industrial Science and Technology, Ministry of International Trade and Industry, Japan, with the following accession numbers.

Pseudomonas putida TS-15001: FERM-P No. 6035 (now FERM BP 159)
Alcaligenes faecalis TS-15002: FERM-P No. 6036 (now FERM BP 160)
Torulopsis candida TS-15101: FERM-P No. 6037 (now FERM BP 161)
Rhodotorula glutinis TS-15103: FERM-P No. 6038 (now FERM BP 162)
Sporobolomyces odorus TS-15105: FERM-P No. 6039 (now FERM BP 163)

An ordinary nutrient medium containing a carbon source, a nitrogen source, an organic nutrient source and an inorganic nutrient source can be used for culturing the above-mentioned microorganisms.

As the carbon source, there can be mentioned carbohydrates such as glucose, sucrose and molasses, and organic acids and their salts such as tartaric acid, fumaric acid, maleic acid and malic acid. As the nitrogen source, there may be used compounds customarily used for ordinary fermentation, for example, inorganic nitrogen compounds such as ammonium sulfate, ammonium chloride, ammonia, ammonium phosphate and ammonium nitrate, and organic nitrogen compounds such as urea, corn steep liquor, casein, peptone, yeast extract and meat extract.

As the inorganic nutrient source, there can be used, for example, calcium salts, magnesium salts, potassium salts, phosphates, iron salts, manganese salts, zinc salts and copper salts.

Incidentally, since Torulopsis candida TS-15101 is a biotin-requiring strain, when this strain is used, biotin or a biotin-containing compound is added to the culture medium.

Culturing of the foregoing microorganisms can be carried out according to customary procedures known for the respective species.

For example, in case of bacteria such as Pseudomonas putida TS-151001 and Alcaligenes faecalis TS-15002, culturing is aerobically carried out in a shaken or submerged culture at a temperature of about 20° to about 40° C., preferably about 25° to about 38° C., and a pH value of about 5 to about 9, preferably about 5.5 to about 7.5. In case of yeasts such as Torulopsis candida TS-15101, Rhodotorula glutinis TS-15103 and sporobolomyces odorus TS-15105, culturing is carried out aerobically in a shaken or submerged culture, as in case of the bactera, but at a temperature of about 15° to about 35° C., preferably about 20° to about 30° C., and a pH value of about 3 to about 8.2, preferably about 4 to about 7.5.

Incidentally, if a small amount of α-APE or a lower alkyl ester of phenylalanine is incorporated in the culture medium, the α-APE-producing activity of the obtained culture of the microorganism or the treated culture product thereof can be increased.

By the "culture of the microorganism" and the "treated culture product thereof" used herein is meant a liquid culture obtained by culturing a miroorganism belonging to the above-mentioned genus, cells collected from this liquid culture, washed cells, dried cells or pulverized cells, obtained by treating the culture or recovered cell, digested cells obtained by autolysis, a lytic product of the cells by means of, for example, an ultrasonic treatment, or an immobilized product thereof. Moreover, an enzymatic protein fraction obtained from such culture product is included.

The separation of cells from the liquid culture and the treatment of the separated cells can easily be accomplished according to customary procedures.

According to the present invention, the above-mentioned culture of the microorganism or the treated culture product thereof may be contacted with L-aspartic acid and a lower alkyl ester of L-phenylalanine in an aqueous solution. The present invention may also be carried out by incorporating L-aspartic acid and a lower alkyl ester of L-phenylalanine into the culture medium in the midway of the culturing, and continuing the culturing whereby the culture of the microorganism is contacted with the added two compounds.

The concentrations of L-aspartic acid and the lower alkyl ester of L-phenylalanine at the time of the contact with the culture of the microorganism or the treated culture product thereof are not particularly limited, but each of these concentrations is ordinarily in the range of from about 1% by weight to the solubility limit and preferably in the range of from about 5% by weight to about 40% by weight, based on the weight of the reaction medium.

The amount of the culture of the microorganism or the treated culture product thereof used is not particularly limited, but ordinarily, the culture of the microorganism or the treated product thereof is used ordinarily in an amount of about 10 to about 1000 g of wet cells, preferably about 50 to about 500 g of wet cells, based on the molarity of the substrate which is present in the lower concentration.

The reaction temperature may be in the range of from about 10° to about 50° C., preferably about 25° to about 40° C., and the pH value of the liquid reaction mixture may be in the range of from about 4 to about 7, preferably about 5 to about 6. The reaction time is not particularly critical, but it is ordinarily preferable that the reaction be conducted from about 1 to about 40 hours, preferably for about 10 to about 20 hours.

As the lower alkyl group in the lower alkyl ester of L-phenylalanine used in the present invention, there can be mentioned methyl, ethyl and isopropyl groups. D-isomers of aspartic acid and the lower alkyl ester of phenylalanine are not used in the present invention, but since the D-isomers do not participate in the reaction, racemic mixtures may be used instead of the L-isomers.

The formed α-APE can be separated and purified according to known separating and purifying means. For example, when the liquid reaction product contains solids such as cells, the solids are separated by centrifugal separation or filtration, and if necessary, a protein-removing treatment is carried out and the α-APE is purified and isolated by conventional separating and purifying means such as column chromatography, thin layer chromatography, crystallization or drying under reduced pressure.

According to the present invention, the amino group of L-aspartic acid used as the starting compound need not be protected, and L-aspartic acid can directly be used for the reaction. Furthermore, since the biochemical reaction is utilized, even if a racemic mixture is used as the starting material, the LL-isomer of α-APE can be prepared selectively. Moreover, β-APE is essentially not formed as a by-product.

The present invention will not be described in detail with reference to the following Examples. Incidentally, in these Examples, all of "%" are by weight.

EXAMPLE 1

A mini-jar type fermentation tank having a capacity of 2 liters was charged with 1.0 l of a culture medium (having a pH value of 5.5) comprising 2% of ammonium fumarate, 0.1% of monopotassium dihydrogenphosphate, 0.1% of dipotassium monohydrogenphosphate, 0.05% of magnesium sulfate heptahydrate, 0.01% of ferric sulfate heptahydrate, 0.01% of manganese chloride and 0.01% of sodium chloride, with the balance water, and sterilization was carried out at 120° C. for 15 minutes.

This culture medium was inoculated with 50 ml of a liquid preculture obtained by culturing Pseudomonas putida TS-15001 in a culture medium (having a pH value of 5.5) having the same compositions as described above at 37° C. for 16 hours. Culturing was carried out under stirring and aeration at a temperature of 37° C., a stirrer rotation number of 500 rpm and an aeration rate of 1 liter of air per minute while adding an aqueous 2N—HCl solution and an aqueous 2N—NaOH solution so that the pH value was maintained in a range of 5.5 to 6.0 during the culturing period.

After culturing was conducted for 16 hours, a part (500 ml) of the obtained liquid culture was subjected to centrifugal separation to collect 5 g of wet cells. The collected cells were suspended in 25 ml of a 1/50M phosphate buffer solution (having a pH value of 5.5). The suspension was incorporated in 25 ml of an aqueous solution containing 3.3 g of L-aspartic acid and 4.5 g of a methyl ester of L-phenylalanine and the mixture was maintained at 37° C. for 16 hours under shaking to effect the reaction.

After completion of the reaction, the liquid reaction mixture was subjected to centrifugal separation at 15° C. and 10,000 rpm for 30 minutes to remove the cells. The obtained supernatant was fractionated by column chromatography (utilizing a column packed with a packing marketted under the tradename of "Toyo Pearl 55F" supplied by Toyo Soda Manufacturing Co., Ltd. and using water/ethanol (80/20 volume ratio) as an eluting solution, and a fraction containing α-L-aspartyl-L-phenylalanine methyl ester was concentrated under reduced pressure to obtain 100 mg of a white powder. The elementary analysis results and physicochemical properties of the powder were as follows.

| | Elementary analysis (%): | |
|---|---|---|
| | Found | Calculated as α-L-aspartyl-L-phenylalanine methyl ester |
| C | 56.81 | 57.14 |
| H | 6.02 | 6.12 |
| N | 9.55 | 9.52 |

Melting point: 235° to 236° (decomposition).
Specific rotatory power: $[\alpha]_D^{25} + 32.0$ (c=1.0, acetic acid).

The molecular weight of a product obtained by trifluoroacetylating the amino group and methylating the carboxyl group was 404.

The above-mentioned powdery product was subjected to thin layer chromatography, high-speed liquid chromatography and analysis utilizing an amino acid analyzer by using L-phenylalanyl-L-phenylalanine, a methyl ester of L-phenylalanyl-L-phenylalanine, diketopiperazine, L-phenylalanine, a methyl ester of L-phenylalanine, L-aspartic acid, L-aspartyl-L-phenylalanine, L-aspartyl-L-aspartic acid, α-L-aspartyl-L-phenylalanine methyl ester and β-L-aspartyl-L-phenylalanine methyl ester as reference substances. Furthermore, a product obtained by methylation of the above powder by hydrochloric acid-methanol and a product obtained by trifluoroacetylation of the above powder by methyl trifluoroacetate were subjected to gas chromatography analysis and gas chromatography/mass spectrography analysis. From the results of these analyses, the above-mentioned powdery product was identified as α-L-aspartyl-L-phenylalanine methyl ester.

EXAMPLES 2 THROUGH 5

A cell suspension was obtained by carrying out the culturing and the separation of cells in the same manner as described in Example 1. The suspension was incorporated in 25 ml of an aqueous solution containing L-aspartic acid and a methyl ester of L-phenylalanine in amounts shown in Table 1, and reaction was carried out under conditions shown in Table 1 to obtain a white powder of α-L-aspartyl-L-phenylalanine methyl ester in an amount shown in Table 1.

TABLE 1

| Example No. | Amounts (g) of reaction in 25 ml of starting aqueous solution | | Reaction conditions | | | Yield (mg) of α-L-aspartyl-L-phenylalanine methyl ester |
|---|---|---|---|---|---|---|
| | L-Aspartic acid | Methyl ester of L-phenylalanine | PH value | Temperature (°C.) | Time (hours) | |
| 2 | 1.0 | 4.5 | 5.5 | 37 | 16 | 60 |
| 3 | 3.3 | 2.0 | 5.5 | 25 | 16 | 30 |
| 4 | 3.3 | 4.5 | 6.0 | 37 | 16 | 80 |
| 5 | 5.0 | 10.0 | 5.0 | 40 | 16 | 80 |

EXAMPLE 6

A cell suspension was obtained by carrying out the culturing and the separation of cells in the same manner as described in Example 1. The reaction was carried out in the same manner as described in Example 1 except that 25 ml of an aqueous solution containing 3.3 g of monosodium DL-aspartate and 4.5 g of a hydrochloride of a methyl ester of DL-phenylalanine was used instead of 25 ml of the aqueous solution of 3.3 g of L-aspartic acid and 4.5 g of the methyl ester of L-phenylalanine, to obtain 50 mg of α-L-aspartyl-L-phenylalanine methyl ester.

EXAMPLE 7

The procedures of Eample 1 were repeated in the same manner except that *Alcaligenes faecalis* TS-15002 was used instead of *Pseudomonas putida* TS-15001, to obtain 80 mg of a white powder of a methyl ester of α-L-aspartyl-L-phenylalanine.

EXAMPLE 8

A mini-jar type fermentation tank having a capacity of 2 liters was charged with a culture medium (having a pH value of 5.0) comprising 1.0% of glucose, 1.0% of ammonium fumarate, 0.1% of monopotassium dihydrogenphosphate, 0.1% of dipotassium monohydrogenphosphate, 0.05% of magnesium sulfate heptahydrate, 0.01% of ferric sulfate heptahydrate, 0.01% of manganese chloride and 0.01% of sodium chloride, with the balance water, and sterilization was carried out at 120° C. for 15 minutes.

The sterilized culture medium was inoculated with 50 ml of a liquid preculture obtained by culturing *Rhodotorrula glutinis* TS-15103 in a culture medium (having a pH value of 5.0) having the same composition as described above at 30° C. for 24 hours. Culturing was carried out under aeration and stirring at a culturing temperature of 30° C., a stirrer rotation number of 500 rpm and an aeration rate of 1 l of air per minute while adding an aqueous 2N—HCl solution and an aqueous 2N—NaOH solution so that the pH value was maintained in a range of 5.0 to 5.5 during the culturing period. After the culturing was conducted for 40 hours, a part (500 ml) of the liquid culture was subjected to centrifugal separation to obtain 5 g of wet cells.

By using the so recovered cells, L-aspartic acid was reacted with a methyl ester of L-phenylanaline in the same manner as described in Example 1, to obtain 80 mg of α-L-aspartyl-L-phenylalanine methyl ester in the form of a white powder.

EXAMPLE 9

The procedures of Example 8 were repeated in the same manner except that *Sporobolomyces odorus* TS-15105 was used instead of *Rhodotorula glutinis* TS-15103, to obtain 70 mg of α-L-aspartyl-L-phenylalanine methyl ester in the form of a white powder.

EXAMPLE 10

A mini-jar type fermentation tank having a capacity of 2 liters was charged with 1.0 l of a culture medium (having a pH value of 5.0) comprising 1.0% of glucose, 1.0% of ammonium fumarate, 0.1% of monopotassium dihydrogenphosphate, 0.1% of dipotassium monohydrogenphosphate, 0.05% of magnesium sulfate heptahydrate, 0.01% of ferric sulfate heptahydrate, 0.01% of manganese chloride, 0.01% of sodium chloride and $0.5 \times 10^{-6}$% of biotin, with the balance water, and sterilization was carried out at 120° C. for 15 minutes.

The sterilized culture medium was inoculated with 50 ml of a liquid preculture obtained by culturing *Torulopsis candida* TS-15101 in a culture medium having the same composition as described above at 30° C. for 24 hours. Culturing was carried out unde aeration and stirring at a culturing temperature of 30° C., a stirrer rotation number of 500 rpm and an aeration rate of 1 l of air per minute while adding an aqueous 2N—HCl solution and an aqueous 2N—NaOH solution so that the pH value was maintained in a range of 5.0 to 5.5 during the culturing period.

After the culturing was conducted for 40 hours, a part (500 ml) of the culture liquid was subjected to centrifugal separation to collect cells, and the cells were suspended in distilled water to form 10 ml of the suspension. Then, 1.9 g of acrylic amide, 0.1 g of N,N'-methylene-bis-acrylamide, 0.5 ml of an aqueous 20% solution of β-dimethylaminopropionitrile and 2 g of ammonium persulfate were added to the suspension, and the mixture was allowed to stand still at room temperature for 10 minutes. The reaction product was pulverized and washed with distilled water to obtain 14 g of immobilized cells.

Then, 10 g of the so-obtained immobilized cells were incorporated in 25 ml of an aqueous solution containing 3.3 g of L-aspartic acid and 4.5 g of a methyl ester of L-phenylalanine and having a pH value of 5.5, and reaction was carried out at 37° C. for 18 hours under shaking. Solids were removed by centrifugal separation, and the remaining aqueous solution was treated in the same manner as described in Example 1, to obtain 45 mg of α-L-aspartyl-L-phenylalanine methyl ester in the form of a white powder.

EXAMPLE 11

In a culture medium having the same composition as that of the culture medium used in Example 1, *Pseudomonas putida* TS-15001 was cultured under the same conditions as those adopted in Example 1. A part (500 ml) of the culture liquid was subjected to centrifugal separation to collect 5 g of wet cells, and the cells were suspended in 25 ml of a 1/50M phosphate buffer solution. The cell suspension was subjected to an ultrasonic vibration treatment at 5° C. for 15 minutes to effect the lysis of the cells. The lytic cell suspension was subjected to centrifugal separation at 5° C. and 10,000 rpm for 15 minutes. The obtained supernatant was incorporated in a time shown in Table 2 to effect reaction of the reactants.

The resulting liquid reaction mixture was subjected to centrifugal separation at 15° C. and 10,000 rpm for 30 minutes to remove cells and solids. The obtained supernatant was treated in the same manner as described in Example 1, to obtain a white powder of a methyl ester of α-L-aspartyl-L-phenylalanine in an amount indicated in Table 2.

TABLE 2

| Example No. | Microorganism used | Culturing conditions and culturing time | pH Value of reaction mixture and reaction time | Yield (g) of α-L-aspartyl-L-phenyl-alanine methyl ester |
|---|---|---|---|---|
| 13 | Pseudomonas putida TS-15001 | Example 1, 16 hours | 6.0, 8 hours | 1.2 |
| 14 | Alcaligenes faecalis TS-15002 | Example 1, 16 hours | 6.0, 8 hours | 1.2 |
| 15 | Torulopsis candida TS-15101 | Example 10, 24 hours | 5.5, 8 hours | 1.5 |
| 16 | Rhodotorula glutinis TS-15103 | Example 8, 24 hours | 5.5, 8 hours | 1.2 |
| 17 | Sporobolomyces odorus TS-15105 | Example 8, 24 hours | 5.5, 8 hours | 1.5 |

25 ml of an aqueous solution containing 3.3 g of L-aspartic acid and 4.5 g of a methyl ester of L-phenylalanine and the mixture was maintained at 37° C. under shaking for 16 hours.

The post treatments were conducted in the same manner as described in Example 1, to obtain 70 mg of L-aspartyl-L-phenylalanine methyl ester in the form of a white powder.

EXAMPLE 12

The procedures of Example 1 were repeated in the same manner except that an ethyl ester of L-phenylalanine was used instead of the methyl ester of L-phenylalanine, to obtain 65 mg of α-L-aspartyl-L-phenylalanine ethyl ester in the form of a white powder.

| | Elementary analysis (%): | |
|---|---|---|
| | Found | Calculated as -L-aspartyl-L-phenylalanine ethyl ester |
| C | 58.53 | 58.43 |
| H | 6.65 | 6.54 |
| N | 9.12 | 9.09 |

Melting point: 244° to 246° C. (decomposition).

Specific rotatory power: $[\alpha]_D^{25} -6.0$ (C=1, methanol).

Molecular weight of product obtained by trifluoromethylation of amino group and methylation of carboxyl group: 418.

EXAMPLES 13 THROUGH 17

The microorganisms shown in Table 2 were cultured under conditions of the Examples indicated in Table 2.

The culturing was conducted for a time shown in Table 2, and 200 ml of an aqueous solution having a pH value shown in Table 2 and containing 70 g of L-aspartic acid and 90 g of a methyl ester of L-phenylalanine was added to the culture under sterilized conditions. Then, the mixture was subjected to further culturing for

We claim:

1. A process for preparing an aspartylphenylalanine alkyl ester, which comprises:
   (1) contacting a liquid culture, cells or a lytic product of cells of a microorganism selected from the group consisting of Pseudomonas putida (FERM BP 159), Alcaligenes faecalis (FERM BP 160), Torulopsis candida (FERM BP 161), Rhodotorula glutinis (FERM BP 162) and Sporobolomyces odorus (FERM BP 163), said microorganism being capable of producing α-L-aspartyl-L-phenylalanine lower alkyl ester from L-aspartic acid and a lower alkyl ester of L-phenylalanine, with L-aspartic acid and a lower alkyl ester of L-phenylalanine in an aqueous medium at a pH from about 4 to about 7; and
   (2) recovering the aspartylphenylalanine alkyl ester so produced.

2. A process according to claim 1, wherein the culture of the microorganism is cells of the microorganism.

3. A process according to claim 1 wherein the treated culture product of the microorganism is immobilized cells.

4. A process according to claim 1, wherein the treated culture product of the microorganism is a lytic product of the microorganism.

5. A process according to claim 1, wherein the lower alkyl ester of L-phenylalanine is a methyl or ethyl ester and the α-L-aspartyl-L-phenylalanine lower alkyl ester is α-L-aspartyl-L-phenylalanine methyl ester or α-L-aspartyl-L-phenylalanine ethyl ester.

6. A process according to claim 1, wherein the microorganism is Pseudomonas putida FERM BP 159.

7. A process according to claim 1, wherein the microorganism is Alcaligenes faecalis FERM BP 160.

8. A process according to claim 1, wherein the microorganism is Torulopsis candida FERM BP 161.

9. A process according to claim 1, wherein the microorganism is Rhodotorula glutinis FERM BP 162.

10. A process according to claim 1, wherein the microorganism is Sporobolomyces odorus FERM BP 163.

* * * * *